(12) United States Patent
Batzinger et al.

(10) Patent No.: US 8,183,493 B2
(45) Date of Patent: May 22, 2012

(54) ULTRASONIC SYSTEM FOR MONITORING A WELD OPERATION

(75) Inventors: Thomas James Batzinger, Burnt Hills, NY (US); Waseem I. Faidi, Clifton Park, NY (US); Sivaramanivas Ramaswamy, Bangalore (IN); Manoj Kumar Koyithitta Meethal, Annur (IN); York Oberdoerfer, NRW (DE); Gerhard Splitt, NRW (DE); Werner Roye, NRW (DE); Johannes Buechler, NRW (DE); Rajagopalan Chandrasekharan, Bangalore (IN)

(73) Assignee: General Electric Company, Niskayuna, NY (US)

( * ) Notice: Subject to any disclaimer, the term of this patent is extended or adjusted under 35 U.S.C. 154(b) by 1090 days.

(21) Appl. No.: 11/237,258

(22) Filed: Sep. 28, 2005

(65) Prior Publication Data

US 2007/0068907 A1     Mar. 29, 2007

(51) Int. Cl.
*B23K 11/25* (2006.01)
*G01M 7/00* (2006.01)

(52) U.S. Cl. ............ 219/109; 73/588; 73/602; 219/91.1

(58) Field of Classification Search ............... 219/109, 219/91.1, 110; 73/588, 599, 600, 602, 618, 73/597; 228/1.1, 110
See application file for complete search history.

(56) References Cited

U.S. PATENT DOCUMENTS

| | | | | |
|---|---|---|---|---|
| 3,302,454 A * | 2/1967 | Kleesattel | | 73/573 |
| 3,410,983 A * | 11/1968 | Deutsch et al. | | 219/109 |
| 3,726,130 A * | 4/1973 | Hurlebaus | | 73/629 |
| 4,596,917 A * | 6/1986 | Nied et al. | | 219/109 |
| 5,222,396 A * | 6/1993 | Takata et al. | | 73/618 |
| 5,920,014 A * | 7/1999 | Waschkies | | 73/597 |
| 6,023,632 A * | 2/2000 | Wilk | | 600/407 |
| 6,425,906 B1 * | 7/2002 | Young et al. | | 606/169 |
| 7,036,376 B2 * | 5/2006 | Arndt | | 73/599 |
| 7,089,099 B2 * | 8/2006 | Shostak et al. | | 701/32 |
| 7,203,133 B1 * | 4/2007 | Stumm et al. | | 73/597 |
| 2004/0094517 A1 * | 5/2004 | Arndt et al. | | 219/109 |
| 2004/0134970 A1 | 7/2004 | Den Boer et al. | | |
| 2004/0206728 A1 * | 10/2004 | Platte et al. | | 219/109 |
| 2005/0049546 A1 * | 3/2005 | Messerly et al. | | 604/22 |
| 2005/0223807 A1 * | 10/2005 | Bardoux et al. | | 73/598 |
| 2006/0076321 A1 * | 4/2006 | Maev et al. | | 219/109 |

(Continued)

FOREIGN PATENT DOCUMENTS

JP     01118375 A   *   5/1989

(Continued)

OTHER PUBLICATIONS

Lott L. A., "Ultrasonic Detection of Molten/Solid Interfaces of Weld Pools", Mar. 1984, Materials Evaluation, Columbus, OH, US, pp. 337-341, XP009060516, ISSN: 0025-5327.

(Continued)

*Primary Examiner* — Geoffrey S Evans
(74) *Attorney, Agent, or Firm* — Fletcher Yoder, PC

(57) ABSTRACT

A system for monitoring a weld operation is provided. The system includes an ultrasonic wave generator adapted to deliver an ultrasonic wave to a target material during the weld operation and an ultrasonic receiver adapted to receive the ultrasonic wave propagated through the target material. The system also includes a signal processor adapted to determine a quality level of a weld created during the weld operation by extracting data corresponding to a torsional mode from the ultrasonic wave and comparing the data to a profile that corresponds to an acceptable quality level.

13 Claims, 6 Drawing Sheets

U.S. PATENT DOCUMENTS

2006/0260403 A1 * 11/2006 Waschkies ..................... 73/588

FOREIGN PATENT DOCUMENTS

| WO | WO 01/11353 | | 2/2001 |
| WO | WO-01/11353 | A2 * | 2/2001 |
| WO | WO 0218088 | A1 * | 3/2002 |
| WO | WO 03106994 | A1 * | 12/2003 |

OTHER PUBLICATIONS

Search Report of Application No. CN200610063929.4 Dated Mar. 2, 2010; 3 Pages.

Rose, Joseph L.; "A Baseline and Vision of Ultrasonic Guided Wave Inspection Potential", Journal of Pressure Vessel Technology, Aug. 2002; vol. 124, pp. 273-282.

* cited by examiner

ULTRASONIC SYSTEM FOR MONITORING A WELD OPERATION

BACKGROUND

The invention relates generally to a technique for monitoring a weld operation, and more particularly, to monitoring a quality level of a weld during the weld operation.

Various types of welding operations are known and are in use. For example, two or more metal sheets may be welded by a spot welding operation. Spot welding utilizes a spot welding machine that includes two copper electrodes held in jaws of the spot welding machine. The material to be welded is clamped between the two electrodes. Typically, a pressure may be applied to hold the electrodes together and a flow of electric current is introduced through the electrodes and the material. Further, the resistance of the material being welded is substantially higher than that of the electrodes. As a result, enough heat is being generated to melt the metal. The pressure on the electrodes forces the molten spots in the two pieces of metal to unite and this pressure is held to facilitate the solidification of the metal. It is desirable to determine the quality of the weld generated through the weld operation to ensure the structural integrity of the welded systems such as automotive frames.

Unfortunately, the present weld monitoring techniques are ineffective to determine the weld quality during the weld operation. In certain systems, excess spot welds are installed in components to ensure the structural integrity of the welded system. Such redundant welds lead to relatively higher process time and additional costs for the manufacturers. Further, excess welds in the system also increase the possibility for corrosion zones on the final product.

In certain systems, destructive testing may be employed to determine the quality of the weld. Typically, the materials joined by the weld process are separated by a hammer and a chisel to assess the strength of the weld and of the material surrounding the weld. Moreover, such destructive testing may be performed on a periodic basis to determine the quality of the weld process. Such testing is relatively time consuming and also leads to material waste.

In certain other systems, offline ultrasonic systems have been used to provide an indication of the weld quality. However, these systems provide an inspection of the weld quality after the process is completed and the weld nugget has solidified. Such systems do not provide information about the weld quality during the weld operation. Further, the existing ultrasonic systems may require a relatively large time for inspecting the weld quality of all welds of a component.

Accordingly, it would be desirable to develop a technique for monitoring the weld operation. More specifically, it would be desirable to develop a technique for real-time monitoring of the quality of the weld created during the weld operation process.

BRIEF DESCRIPTION

Briefly, according to one embodiment of the invention, a system for monitoring a weld operation is provided. The system includes an ultrasonic wave generator adapted to deliver an ultrasonic wave to a target material during the weld operation and an ultrasonic receiver adapted to receive the ultrasonic wave propagated through the target material. The system also includes a signal processor adapted to determine a quality level of a weld created during the weld operation by extracting data corresponding to a torsional mode from the ultrasonic wave and comparing the data to a profile that corresponds to an acceptable quality level.

In another embodiment, a method of monitoring a weld quality in a weld operation is provided. The method includes delivering an ultrasonic wave to a target material during the weld operation and receiving the ultrasonic wave propagated through the target material. The method also includes extracting data corresponding to a torsional mode of the ultrasonic wave and evaluating the data to determine a quality level of a weld created during the weld operation.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
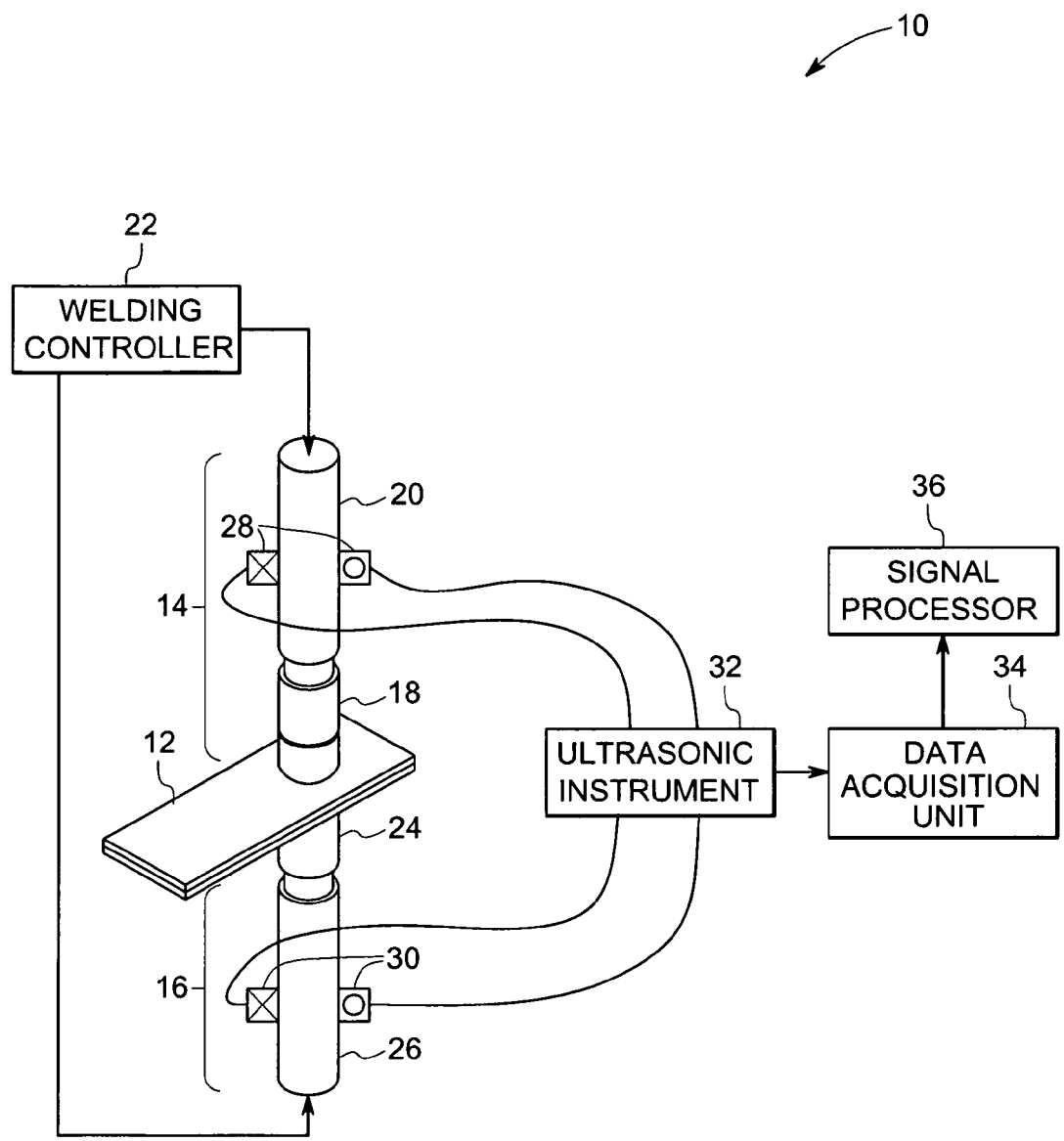
FIG. 1 is a diagrammatical illustration of a system for monitoring a weld operation in accordance with aspects of the present technique.

As discussed in detail below, embodiments of the present technique function to monitor a quality level of a weld during a weld operation such as a spot weld operation. Turning now to drawings and referring first to FIG. 1, a system 10 for monitoring a weld operation for a target material 12 is illustrated. The weld monitoring system 10 includes a first electrode 14 and a second electrode 16. Moreover, the first electrode 14 includes a probe tip 18 that couples directly to the target material 12 and a shank 20 that is coupled to a welding controller 22. Similarly, the second electrode 16 includes a probe tip 24 and a shank 26 that is coupled to the welding controller 22.

In a presently contemplated configuration the system 10 includes an ultrasonic wave generator 28 that is adapted to deliver an ultrasonic wave to the target material 12. Additionally, the system 10 includes an ultrasonic receiver 30 adapted to receive the ultrasonic wave propagated through the target material 12. In the illustrated embodiment, the ultrasonic wave generator 28 is disposed on the welding shank 20 on a first side of the target material 12. Further, the ultrasonic receiver 30 is disposed on the welding shank 26 on a second side that is opposite the first side of the target material 12. In certain embodiments, the ultrasonic generator 28 and the ultrasonic receiver 30 may be disposed on welding clamps of the system 10 for generating torsional guided waves.

In the embodiment illustrated in FIG. 1, the ultrasonic wave generator 28 and the ultrasonic receiver 30 include at least two piezoelectric elements mounted on the welding shanks 20 and 26. In certain embodiments, a single piezoelectric element may be mounted on the welding shanks 20 and 26. The piezoelectric elements are configured to generate torsional guided waves in the welding shanks 20 and 26. Examples of piezoelectric elements include, but are not limited to, piezoelectric materials and piezoelectric composites. In one embodiment, the ultrasonic wave generator 28 and the ultrasonic receiver 30 include electromagnetic acoustic transducers. In an alternate embodiment, the ultrasonic wave generator 28 and the ultrasonic receiver 30 include capacitive micro-machined ultrasound transducers. In certain embodiments, parameters such as a source frequency, an aperture, a location and an angle of incidence are selected to generate the desired torsional guided waves. Moreover, a frequency of the generated torsional guided waves is above 1 MHz. In one embodiment, the frequency of the torsional guided waves is in the range of about 1 MHz to about 2 MHz. As illustrated, the ultrasonic wave generator 28 and the ultrasonic receiver 30 are coupled to an ultrasonic instrument 32 to facilitate generation and receiving of the ultrasonic waves via the ultrasonic wave generator 28 and the ultrasonic receiver 30.

In operation, the target material 12 is clamped between the first and second electrodes 14 and 16 under relatively high pressure. In certain embodiments, the target material 12 includes two or more sheets of metal such as steel and aluminum. Further, a flow of electrical current is introduced through the first and second electrodes 14 and 16 and through the target material 12. As a result, substantial amount of heat is generated to melt the metal. The pressure on the first and second electrodes 14 and 16 forces the molten spots in the two pieces of the target material 12 to unite and this pressure is held to facilitate the solidification of the metal and the formation of the weld between the two pieces of the target material 12. In the illustrated embodiment, the pressure and current applied to the first and second electrodes 14 and 16 is controlled via the welding controller 22. In particular, a piston (not shown) may be employed to apply a desired pressure to the target material 12. Such a piston may be coupled to the first and second electrodes 14 and 16. In an alternate embodiment, a servomotor may be employed to apply a desired pressure to the target material 12. Further, a power supply (not shown) is coupled to the first and second electrodes 14 and 16. Again, the amount of current applied to the first and second electrodes 14 and 16 via the power supply is controlled through the welding controller 22.

As illustrated above, the piezoelectric elements are configured to generate torsional guided waves in the welding shanks 20 and 26. Further, data corresponding to the torsional mode from the ultrasonic wave is utilized to determine a quality level of the created weld. In the illustrated embodiment, the system 10 includes a data acquisition unit 34 to extract the data from the ultrasonic instrument 32. Further, a signal processor 36 is coupled to the data acquisition unit 34 to process the data acquired by the data acquisition unit 34. In a present embodiment, the signal processor 36 extracts the data corresponding to the torsional mode from the ultrasonic wave and compares the extracted data to a profile that corresponds to an acceptable quality level. Thus, the quality of the generated weld is monitored in real-time through the torsional guided waves generated in the system 10 by the piezoelectric elements disposed on the welding shanks 20 and 26. As will be appreciated by one skilled in the art other types of modes of the ultrasonic wave may be monitored to determine the weld quality during the weld operation. Examples of such modes include a longitudinal mode, a flexural mode and so forth.

Figure 2:
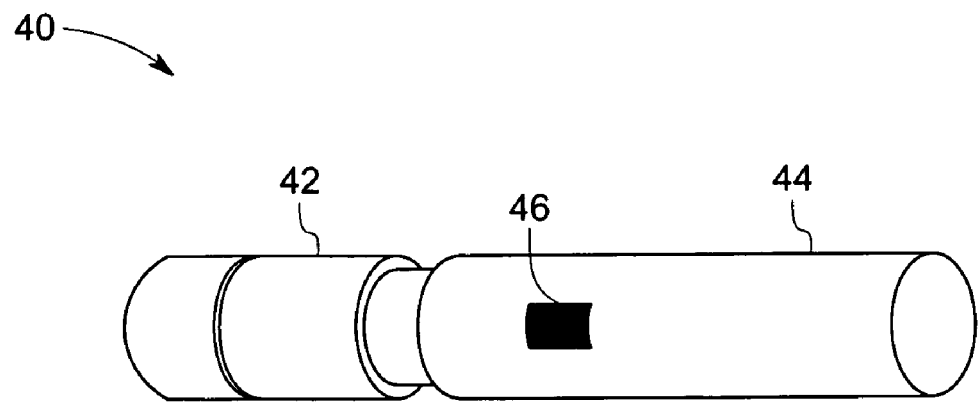
FIG. 2 is a diagrammatical illustration of an exemplary shank and cap assembly employed in the system of FIG. 1 in accordance with aspects of the present technique.

FIG. 2 illustrates an exemplary shank and cap assembly 40 employed in the system 10 of FIG. 1. As illustrated, the assembly 40 includes a welding tip 42 and a welding shank 44. The piezoelectric elements forming the ultrasound wave generator 28 and the ultrasound receiver 30 may be mounted directly on the surface of the welding shank 44. Alternatively, the piezoelectric elements may be mounted on the surface of the welding shank 44 via angle wedges. Further, features such as a flat cutout 46 may be machined on the surface of the welding shank 44 to facilitate the mounting of the piezoelectric elements. In the present embodiment, two or more piezoelectric elements, which are shear probes, are mounted on the surface of the welding shank 44 and oriented such that torsional guided waves are generated in the assembly 40. The torsional wave generation through the piezoelectric elements will be described below with reference to FIG. 3.

Figure 3:
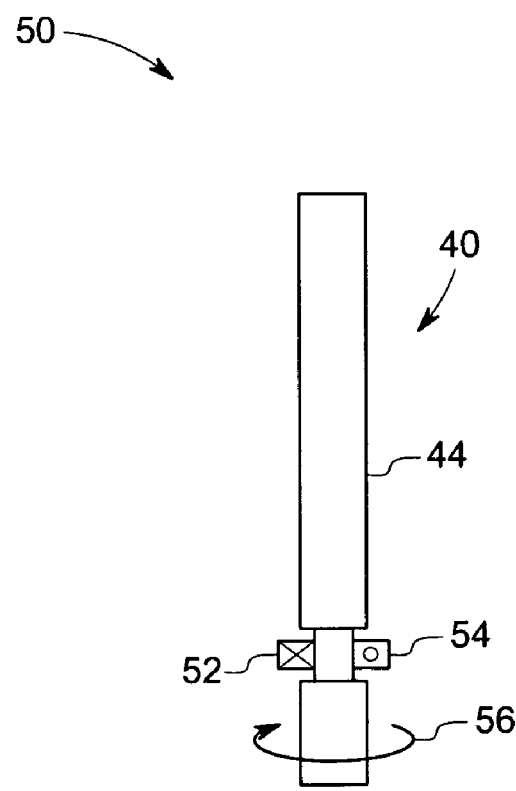
FIG. 3 is a diagrammatical illustration showing a torsional force from an ultrasonic wave generated by the system of FIG. 1 on an exemplary shank and cap in accordance with aspects of the present technique.

FIG. 3 illustrates a torsional force 50 from an ultrasonic wave generated by the system of FIG. 1 on an exemplary shank and cap assembly. In the illustrated embodiment, piezoelectric elements 52 and 54 are mounted on the welding shank 44 and are oriented such that torsional guided waves are generated in the assembly 40. In one embodiment, two piezoelectric elements 52 and 54 may be employed to generate transverse waves in an area of contact between the piezoelectric elements 52 and 54 and the surface of the welding shank 44. Further, the piezoelectric elements 52 and 54 may be mounted on two opposite sides of the welding shank 44 and are excited out of phase such that a torsional guided wave 56 is generated.

The exemplary configuration described above generates torsional guided waves between the tips of the two shanks through the target material to be welded. Further, the signal processor 36 extracts the data corresponding to the torsional mode from the ultrasonic wave and compares the extracted data to a profile that corresponds to an acceptable quality of weld to determine the quality level of the weld created during the weld operation. In one embodiment, the signal processor 36 is configured to determine an amplitude profile corresponding to the torsional mode from the ultrasonic wave as illustrated below with reference to FIGS. 4 and 5.

Figure 4:
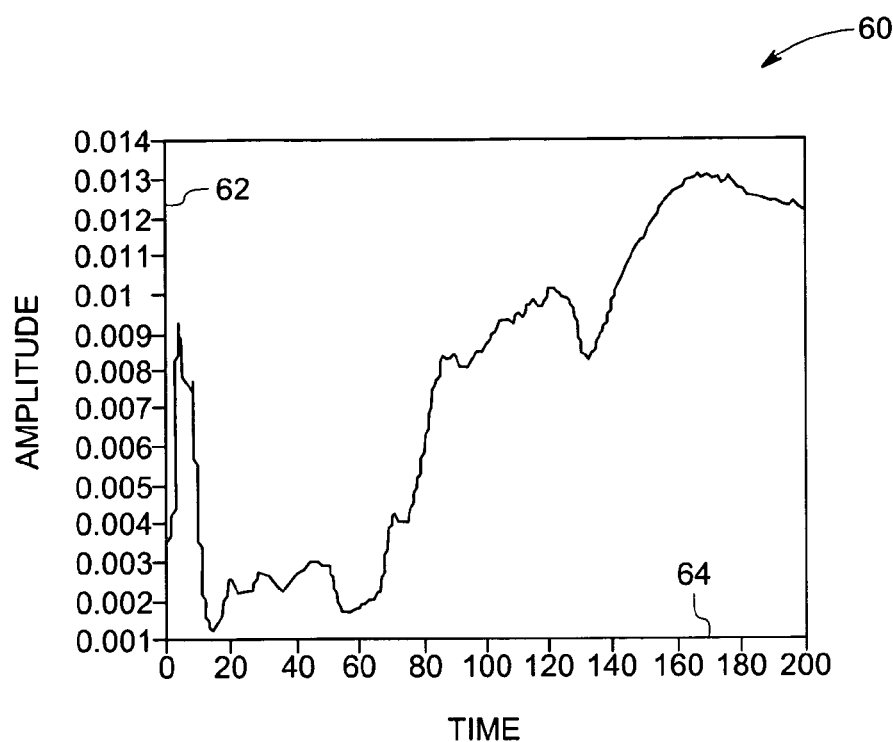
FIG. 4 is an exemplary amplitude profile for a good weld created via the system of FIG. 1 in accordance with aspects of the present technique.
Figure 5:
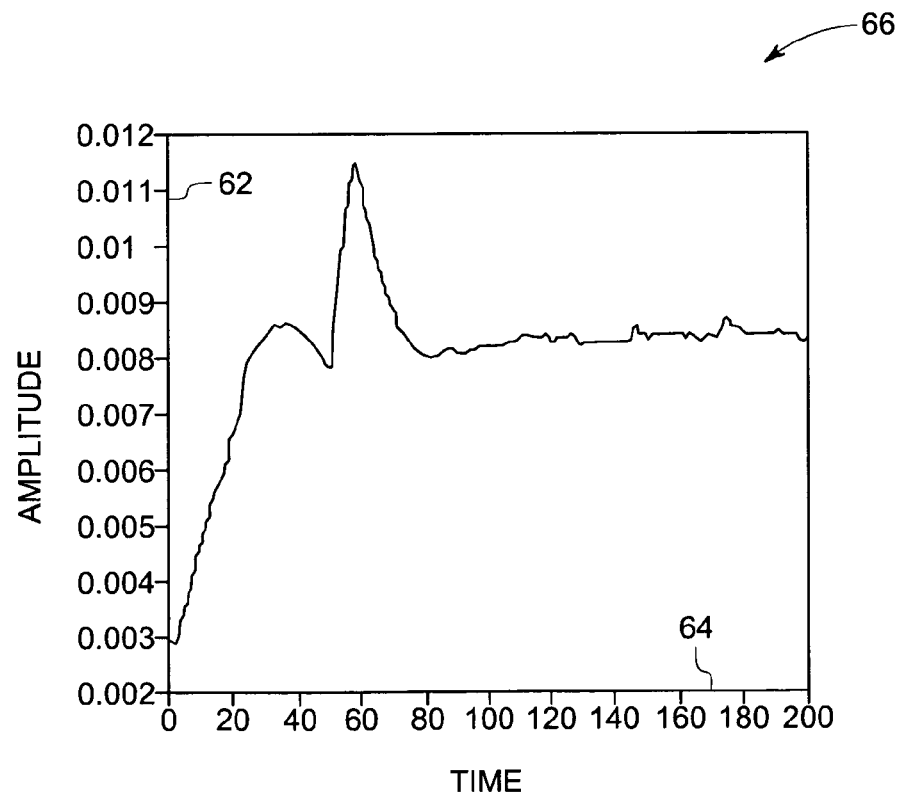
FIG. 5 is an exemplary amplitude profile for a bad weld in accordance with aspects of the present technique.

FIG. 4 illustrates an exemplary amplitude profile 60 for a good weld created via the system 10 of FIG. 1. The ordinate axis of the amplitude profile 60 represents an amplitude 62 of the ultrasonic wave and the abscissa axis represents a welding time 64. In the illustrated embodiment, the data corresponds to ultrasonic waves having a frequency of about 2 MHz for uncoated steel. As illustrated, the amplitude at 2 MHz frequency is reduced over a period of time for a good weld. It should be noted that transmission of torsion is substantially reduced due to the loss of shear modulus of the molten material during the weld operation, which leads to reduction of the amplitude of the signal. FIG. 5 illustrates an exemplary amplitude profile 66 for a bad weld. Again, the data corresponds to ultrasonic waves having a frequency of about 2 MHz for uncoated steel. As can be seen, the amplitude of the ultrasonic wave does not increase over a period of time for a bad weld. Thus, the amplitude profile corresponding to the torsional mode from the ultrasonic wave is indicative of the weld quality. More particularly, the amplitude profile corresponding to the torsional mode from the ultrasonic wave may be compared to a profile that corresponds to an acceptable quality level to determine and monitor the weld quality.

As illustrated above, the signal processor 36 (see FIG. 1) is configured to determine the weld quality level by extracting data corresponding to the torsional mode from the ultrasonic wave and comparing the data to a profile corresponding to an acceptable quality level. In one embodiment, the signal processor 36 employs digital pattern classification for determining the quality level of the weld created during the weld operation. Alternatively, the frequency of the ultrasonic wave may be analyzed by the signal processor 36 to separate the torsional mode from other modes of the ultrasonic wave. Further, the signal processor 36 may employ a time-frequency filter to separate the torsional mode from the other modes of the ultrasonic wave. In certain other embodiments, parameters such as electric current, voltage and the electrode temperatures may be controlled to control the weld quality level.

Figure 6:
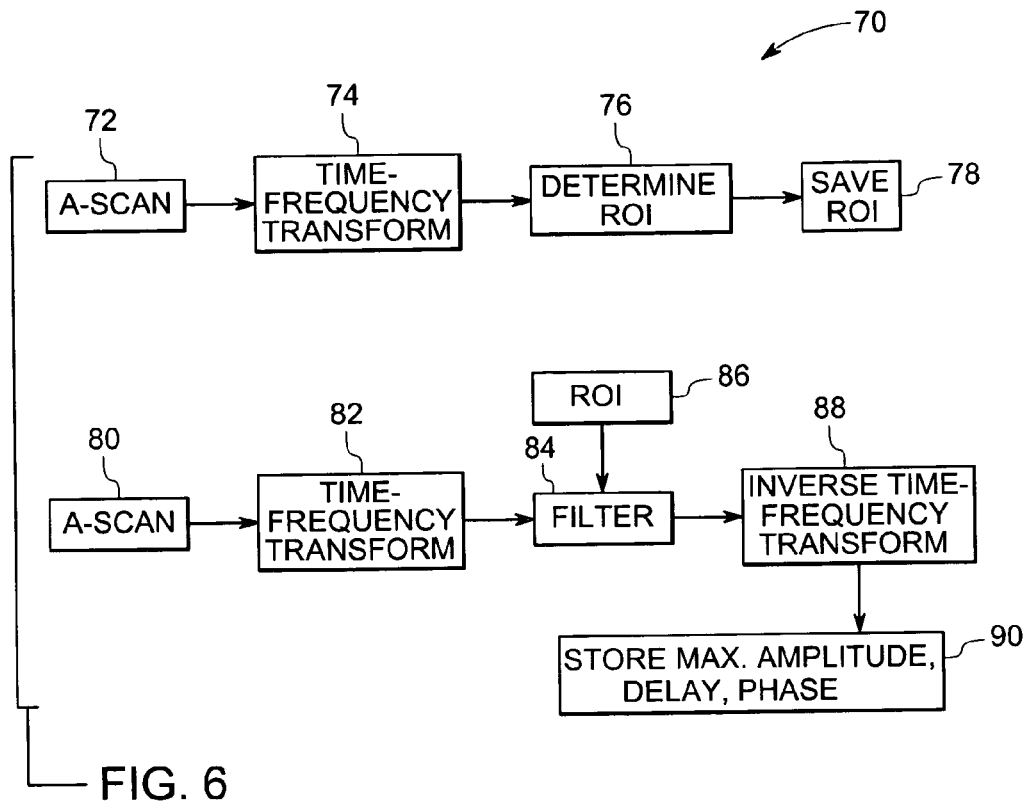
FIG. 6 is a flow diagram showing an exemplary process for manipulating the signals from the system of FIG. 1 to determine a quality level of the weld created during a weld operation.

FIG. 6 is a flow diagram showing an exemplary process 70 for manipulating the signals from the system of FIG. 1 to determine a quality level of the weld created during a weld operation. The process 70 employs time-frequency filter for separating the torsional mode from the ultrasonic wave to facilitate the monitoring of the weld quality. In the illustrated embodiment, an A-scan 72 for the weld is obtained. Further, a time-frequency transform 74 is performed to determine a region of interest (ROI) 76. In this embodiment, the time-frequency transform includes a Short-Time Fourier Transform (STFT). However, other time-frequency distributions are within the scope of this technique. In one embodiment, the time-frequency transform includes Wavelet transform. In a present embodiment, the region of interest 76 is stored for use as a two-dimensional filter mask for subsequent A-scans, as represented by reference numeral 78.

Next, A-scans 80 corresponding to each weld are converted to time-frequency representation by performing a time-frequency transform 82 of the A-scans 80. Subsequently filtering of the time-frequency representation is performed through a filter 84. In the illustrated embodiment, STFT is employed to perform the time-frequency transform. In particular, the filtering is performed by utilizing a ROI 86 that is determined from a previous A-scan 80. Moreover, an inverse time-frequency transform 88 is performed to determine parameters such as maximum amplitude, delay and phase for the ultrasound wave. In this embodiment, the inverse time-frequency transform 88 includes an Inverse Short-Time Fourier Transform (ISTFT). Such parameters are stored for every A-scan acquired for each weld to monitor the weld quality of the weld created during the welding operation, as represented by reference numeral 90.

Figure 7:
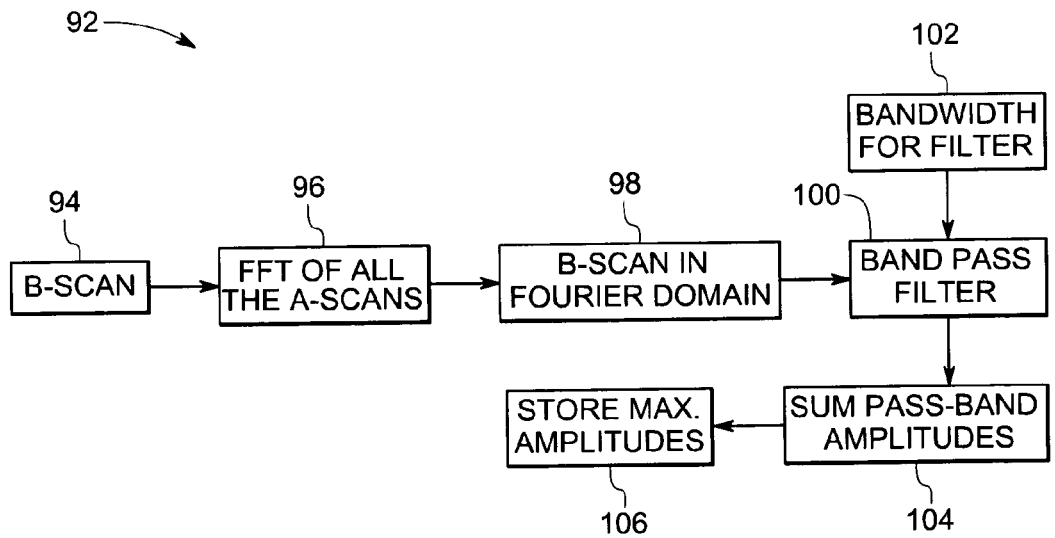
FIG. 7 is a flow diagram showing another exemplary process for manipulating the signals from the system of FIG. 1 to determine a quality level of the weld created during a weld operation.

FIG. 7 is a flow diagram showing another exemplary process 92 for manipulating the signals from the system of FIG. 1 to determine a quality level of the weld created during a weld operation. In the illustrated embodiment, a B-scan 94 is obtained for each weld. Further, the A-scans for all the welds are then converted to the frequency domain by performing a Fast-Fourier-Transformation 96 to obtain a B-scan in the Fourier domain 98. Next, the obtained B-scans 98 are band pass filtered via a band pass filter 100 for a pre-determined bandwidth 102. It should be noted that the desired bandwidth 102 may be specified by an operator of the weld monitoring system 10 (see FIG. 1). Subsequently, pass band amplitudes 104 obtained from the band pass filter 100 are summed and stored for each weld A-scan 94 for monitoring the weld quality as represented by reference numerals 104 and 106 respectively. The above-mentioned process may be repeated to process the signals for each of the A-scans acquired for each weld.

Figure 8:
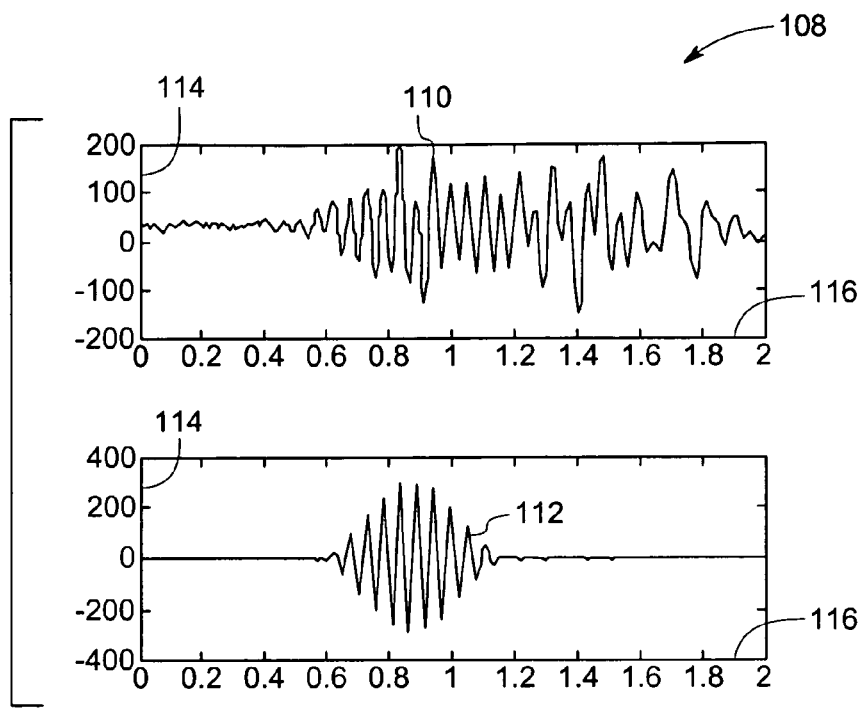
FIG. 8 is an exemplary graph that illustrates raw and filtered signals generated by the process of FIGS. 6 and 7 for a pre-weld condition in accordance with aspects of the present technique.

FIG. 8 is an exemplary graph 108 that illustrates raw and filtered signals 110 and 112 generated by the process such as described above with reference to FIGS. 6 and 7 for a pre-weld condition during a squeeze phase. The ordinate axis 114 represents an amplitude of the signal and the abscissa axis 116 represents a transit time between generated and received signals. In the illustrated embodiment, the raw signal 110 corresponds to a plurality of modes of the ultrasonic wave. For example, the raw signal 110 may correspond to a combination of a torsional wave, an extensional wave and a flexural wave, among others. The raw signal 110 is processed to generate the filtered signal 112 that corresponds to the torsional mode of the ultrasonic wave. In a present embodiment, the filtered signal 112 is indicative of the amplitude profile of a relatively smaller frequency band as compared to the raw signal 110. As illustrated above the raw signal 110 may be filtered by employing time-frequency transform or via frequency-domain transform as described above with reference to FIGS. 6 and 7. However, other filtering techniques are within the scope of this invention.

Figure 9:
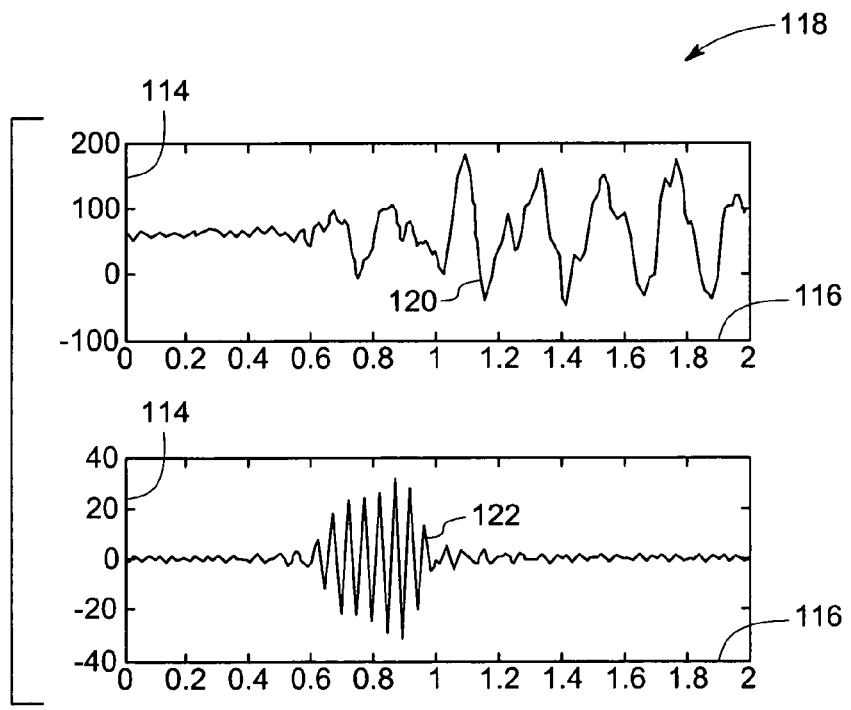
FIG. 9 is an exemplary graph that illustrates raw and filtered signals generated by the process of FIGS. 6 and 7 received during the weld operation in accordance with aspects of the present technique.

FIG. 9 is an exemplary graph 118 that illustrates raw and filtered signals 120 and 122 generated by the process of FIGS. 6 and 7 received during the weld operation for a "current-on" stage. Again, the raw signal 120 is representative of the amplitude profile corresponding to a plurality of modes of the ultrasound wave. The signal processing technique described above is employed to convert the raw signal 120 to the filtered signal 122 that corresponds to the torsional mode during the weld operation. The amplitude of the filtered mode may be monitored to assess the weld quality between different phases of the weld operation. For example, the maximum amplitude of the filtered signal 122 during the pre-weld operation is greater than the maximum amplitude of the filtered signal 112 in a weld operation. The amplitude of the filtered signal of the ultrasonic wave changes over time and is indicative of the weld quality.

Figure 10:
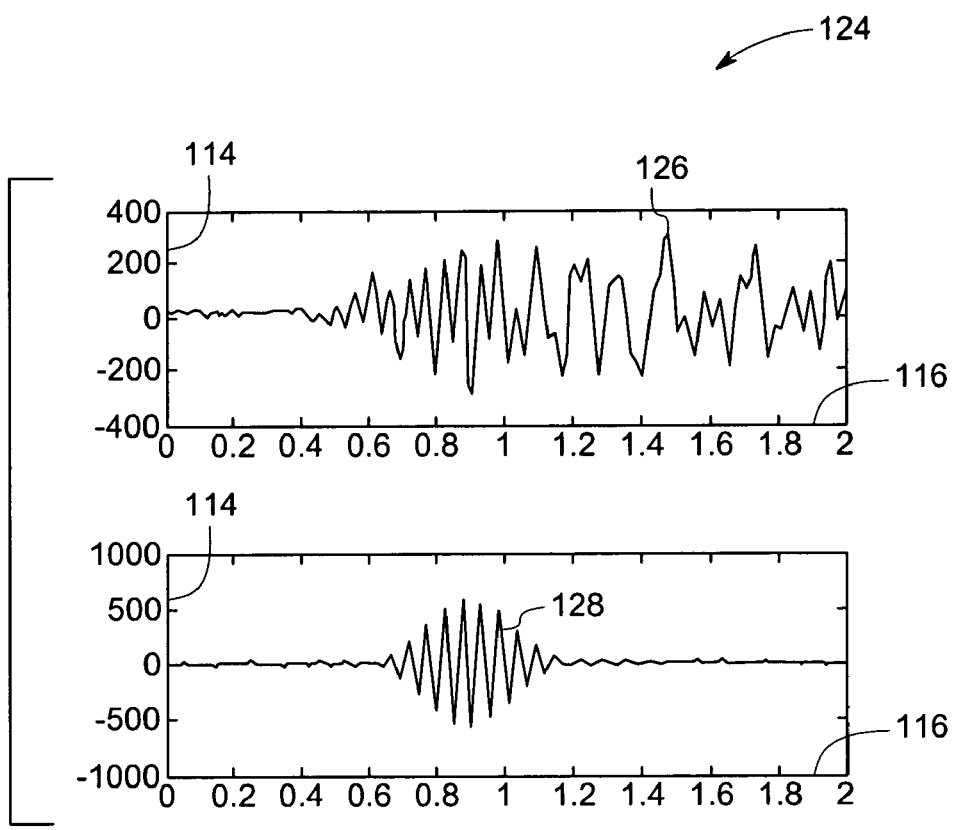
FIG. 10 is an exemplary graph that illustrates raw and filtered signals generated by the process of FIGS. 6 and 7 for a post-weld condition in accordance with aspects of the present technique.

FIG. 10 is another exemplary graph 124 that illustrates raw and filtered signals 126 and 128 generated by the process of FIGS. 6 and 7 for a post-weld condition in a "current-off" stage in accordance with aspects of the present technique. As illustrated, the raw signal 126 for the post-weld condition is processed to determine the filtered signal 128 corresponding to the torsional mode of the ultrasonic wave. Moreover, the maximum amplitude of the filtered signal 126 is monitored to indicate the weld quality. In the illustrated embodiment, the maximum amplitude of the filtered signal 128 for the post-weld condition is substantially greater than as compared to the maximum amplitude of the filtered signal 122 during the weld operation. Thus, by monitoring the amplitude of the filtered signal of the ultrasonic wave for different phases of the welding operation the weld quality of the weld may be determined.

As will be appreciated by those skilled in the art certain other parameters of the filtered signals may be evaluated to determine the quality level of the weld. In one embodiment, the quality level of the weld is determined based on reduction of transmission of the ultrasonic wave through the target material. In an alternate embodiment, the quality level of the weld is determined based on a digital signal pattern classification. In certain embodiments, the time of flight may be monitored for determining the weld quality. Further, the technique may be employed to determine a parameter of the weld created during the weld operation. Examples of such parameter include weld thickness, weld diameter and so forth.

Moreover, a parameter of the welding operation may be controlled based upon the quality level of the weld to achieve an acceptable quality level. In one embodiment, the parameter includes the current applied to the first and second electrodes 14 and 16 (see FIG. 1). In certain embodiments, the parameter includes the amount of pressure applied to the first and second electrodes 14 and 16. In certain other embodiments, the parameter includes time of application of the current or pressure to the first and second electrodes 14 and 16. As noted above, such parameters may be controlled during the weld operation via the welding controller 22 (see FIG. 1).

As will be appreciated by one skilled in the art the weld monitoring system described above may be employed for a closed-loop control of the weld quality for a weld. Thus, the quality of the weld determined via this system may be utilized to control the parameters of the welding operation to achieve an acceptable quality level. Further, the technique may be employed for a feed-forward control of the quality of subsequent welds during the welding operation. The quality of the weld determined for a weld may be utilized to adjust the parameters of the welding operation for controlling the quality of the subsequent welds.

The various aspects of the method described hereinabove have utility in monitoring the weld operation. For example, the technique illustrated above may be employed to monitor the quality level of a weld created during a spot weld operation. As noted above, even more generally, the method described herein may be advantageous for real-time monitoring of the quality of the weld created during the weld operation process. Advantageously, the real-time monitoring of the weld facilitates real-time control of the weld quality.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A system for monitoring a weld operation, comprising:
    a first structure and a second structure configured to be disposed on different sides of a target material;
    an ultrasonic wave generator comprising two or more separate generating elements directly or indirectly coupled to the first structure and adapted to deliver a guided ultrasonic wave to the target material during the weld operation, wherein the two or more separate generating elements are at different angular orientations with respect to the first structure;
    an ultrasonic receiver directly or indirectly coupled to the second structure and adapted to receive the guided ultrasonic wave propagated through the target material; and
    a signal processor adapted to monitor a quality level of a weld by extracting a transmit time versus signal amplitude plot corresponding to a torsional ultrasonic mode by separating the torsional ultrasonic mode from the guided ultrasonic wave and by comparing the extracted plot to a reference transmit time versus amplitude plot that corresponds to an acceptable quality level.

2. The system of claim 1, wherein the first structure comprises a welding shank disposed on a first side of the target material.

3. The system of claim 2, wherein the second structure comprises a second welding shank on a second side that is opposite the first side of the target material.

4. The system of claim 1, wherein the ultrasonic wave generator and the ultrasonic receiver comprise at least two piezoelectric elements mounted on the welding shank, wherein the piezoelectric elements are adapted to generate torsional guided waves in the welding shank.

5. The system of claim 4, wherein the piezoelectric elements comprise piezoelectric materials, or piezoelectric composites.

6. The system of claim 4, wherein a frequency of the torsional guided waves is above 1 MHz.

7. The system of claim 1, wherein the first structure comprises a first portion of a welding clamp and the second structure comprises a second portion of the welding clamp.

8. The system of claim 1, wherein the ultrasonic wave generator and the ultrasonic receiver comprise electromagnetic acoustic transducers, or capacitive micro-machined ultrasound transducers.

9. The system of claim 1, wherein the signal processor employs digital pattern classification for determining the quality level of the weld created during the weld operation.

10. The system of claim 1, wherein the signal processor is configured to analyze the frequency of the ultrasonic wave to separate the torsional mode from other ultrasonic wave modes.

11. The system of claim 1, wherein the signal processor employs a time-frequency filter to separate the torsional mode from the ultrasonic wave.

12. The system of claim 1, further comprising a weld controller adapted to control the quality level of the weld by altering a weld parameter to match a profile of the extracted plot to a profile of the reference plot.

13. A system for monitoring a weld operation, comprising:
    an ultrasonic wave generator comprising two or more distinct generating elements directly or indirectly coupled to a first structure configured to be disposed on a first side of a target material and adapted to be excited out of phase to generate a guided ultrasonic wave, wherein the two or more distinct generating elements are at different angular orientations with respect to the first structure;
    an ultrasonic receiver directly or indirectly coupled to a second structure configured to be disposed on a second side of the target material opposite the first side and adapted to receive the guided ultrasonic wave propagated through the target material; and
    a signal processor adapted to monitor a quality level of a weld by extracting a transmit time versus signal amplitude plot corresponding to a torsional ultrasonic mode by separating the torsional ultrasonic mode from the guided ultrasonic wave and by comparing the extracted plot to a reference transmit time versus amplitude plot that corresponds to an acceptable quality level.

* * * * *